(12) United States Patent
Eriksson et al.

(10) Patent No.: US 8,187,811 B2
(45) Date of Patent: May 29, 2012

(54) POLYMORPHISMS ASSOCIATED WITH PARKINSON'S DISEASE

(75) Inventors: Nicholas Eriksson, Palo Alto, CA (US); Chuong Do, Mountain View, CA (US)

(73) Assignee: 23andMe, Inc., Mountain View, CA (US)

( * ) Notice: Subject to any disclaimer, the term of this patent is extended or adjusted under 35 U.S.C. 154(b) by 0 days.

(21) Appl. No.: 12/956,525

(22) Filed: Nov. 30, 2010

(65) Prior Publication Data

US 2011/0130337 A1    Jun. 2, 2011

Related U.S. Application Data

(60) Provisional application No. 61/265,304, filed on Nov. 30, 2009, provisional application No. 61/359,769, filed on Jun. 29, 2010.

(51) Int. Cl.
*C12Q 1/68* (2006.01)
*C07H 21/00* (2006.01)

(52) U.S. Cl. ...... 435/6.11; 435/6.1; 435/6.12; 536/23.1; 536/24.3; 536/24.33

(58) Field of Classification Search ............ None
See application file for complete search history.

(56) References Cited

U.S. PATENT DOCUMENTS

2006/0257903 A1    11/2006    Akil et al.
2008/0286796 A1    11/2008    Grupe et al.

OTHER PUBLICATIONS dbSNP ss14913242 (First Entry to dbSNP Nov. 13, 2003).*
Satake et al. The 12th ICHG and ASHG 61 Annual Meeting. 2011. p. 393, Abstract 543T.*
Do et al. PLoS Genetics. 2011. 7(6): e1002141.*
Nalls et al. Lancet. 2011. 377: 641-649.*
NCBI Reference SNP Cluster Report: rs10513789. Nov. 2003. [Retrieved from the internet May 2, 2011: <URL: http://www.ncbi.nlm.nih.gov/projects/SNP/snp_ref.cgi?rs=10513789>]; GeneView.
Pankratz et al. Genomewide Association Study for Susceptibility Genes Contributing to Familial Parkinson Disease. National Institutes of Heath—Public Access Author Manuscript. Hum Genet, Jan. 2009; 124(6): 593-605. doi:10.2007/s00439-008-0582-9.

* cited by examiner

*Primary Examiner* — Dave Nguyen
*Assistant Examiner* — Joseph G Dauner
(74) *Attorney, Agent, or Firm* — Van Pelt, Yi & James LLP

(57) ABSTRACT

The invention provides human polymorphisms that are associated with Parkinson's disease (PD). Also disclosed are compositions and methods for use in diagnostics, prognostics, prevention, treatment and/or study of PD.

7 Claims, 8 Drawing Sheets

POLYMORPHISMS ASSOCIATED WITH PARKINSON'S DISEASE

CROSS REFERENCE TO OTHER APPLICATIONS

This application claims priority to U.S. Provisional Patent Application No. 61/265,304 entitled POLYMORPHISMS ASSOCIATED WITH PARKINSON'S DISEASE filed Nov. 30, 2009 and U.S. Provisional Patent Application No. 61/359,769 entitled POLYMORPHISMS ASSOCIATED WITH PARKINSON'S DISEASE filed Jun. 29, 2010 which are incorporated herein by reference for all purposes.

FIELD OF THE INVENTION

The present invention is related to polymorphisms associated with Parkinson's disease. More specifically, the invention is related to compositions, methods and for use in therapeutic and preventative treatment, study, diagnosis and prognosis of Parkinson's disease.

CROSS-REFERENCE TO SEQUENCE LISTING

The sequence listing included in the electronic file submitted herewith as one of the parts of this application, entitled "23MEP023_PD_Sequence_Listing", is incorporated by reference into this application in its entirety. The sequence listing is created on Apr. 19, 2012 and is 3 kilobytes in size.

BACKGROUND OF THE INVENTION

Parkinson's disease (PD) is a progressive degenerative disease of the central nervous system (CNS). PD is characterized by muscle rigidity, tremors, a slowness of physical movement (bradykinesia), impaired balance and coordination, and, in advanced stages, a loss of physical movement (akinesia). Over one million Americans suffer from Parkinson's disease, with the prevalence of approximately 1 in 272 or 0.37% in the United States (US Census Bureau, Population Estimates, 2004).

There is no known cure for PD. Patients are treated with drugs and physical therapy to control the symptoms, but the disease is a progressive disorder and symptoms continue to worsen throughout life. Four major classes of drugs are used to treat PD: Levodopa, direct dopamine agonists, catechol-O-methyltransferase (COMT) inhibitors and anticholinergics. Other types of drugs include selegiline (an MAO-B inhibitor), amantadine (an antiviral agent), vitamin E and hormone replacement therapy. Although these treatments may provide relief from the symptoms of PD, these noncurative drug treatments are often are accompanied by side effects, such as low blood pressure, nausea, constipation, and various psychiatric or behavioral disorders (e.g., hallucinations, depression, and sleep disorders).

While the molecular bases for PD have not been fully elucidated, several genetic regions have been found to be associated with PD. The PARK1 region at 4q21 contains the alpha-synuclein (SNCA) gene. Certain mutations in this gene confer a rare autosomal dominant form of PD (Duvoisin, R. C. (1996), *Recent advances in the genetics of Parkinson's disease*, Adv Neurol 69:33-40; Polymeropoulos et al. (1997) *Mutation in the alpha-synuclein gene identified in families with Parkinson's disease*, Science 276:2045-7; and Kruger et al. (1998) *Ala30Pro mutation in the gene encoding alpha-synuclein in Parkinson's disease*, Nat Genet. 18:106-108). The PARK2 region at 6q25-27 contains the Parkin gene. The loss of function of both copies of the parkin gene confers an autosomal recessive juvenile form of PD (Abbas et al. (1999) *A wide variety of mutation in the parkin gene are responsible for autosomal recessive parkinsonism in Europe*, Hum Mol Genet. 8:567-574; Lucking et al. (1998) *Homozygous deletions in the parkin gene in European and North African families with autosomal recessive juvenile parkinsonism*, Lancet 352:1355-1356; and Lucking et al. (2000) *Association between early-onset Parkinson's disease and mutations in the parkin gene*, N Engl J Med 342:1560-1567). Other regions believed to contain one or more genes associated with PD include PARK3 at 2p13 (autosomal dominant), PARK4 at 4p15 (autosomal dominant; same locus as PARK1), PARK5 at 4p14 (which contains a gene encoding a neuron-specific C-terminal ubiquitin hydrolase), PARK6 at 1p35 (autosomal recessive), PARK7 at 1p36 (which contains the DJ-1 gene; autosomal recessive) and PARK8 at 12p1.2-q13.1 (which contains the LRRK2 gene; autosomal dominant). Additional loci designated PARK9, PARK10, PARK11, PARK12, PARK13, PARK14, PARK15, and PARK16 have also been linked to PD. While the molecular bases for most cases of PD are unclear, the various genetic regions that have been linked to this disease serve to illustrate the potential that the etiology of PD may involve the interaction of a large number of genetic components.

SUMMARY OF THE INVENTION

The present application provides compositions, methods and systems for determining increased or decreased risk or susceptibility of an individual to developing Parkinson's disease (PD). In one aspect, the application provides nucleic acid sequences that may be used to determine the presence or absence of nucleotides at polymorphic sites in an individual's RNA or genomic DNA that are associated with susceptibility to or protection from PD. In another aspect, the application provides a method for identifying a human subject having an increased or decreased susceptibility to PD, including the following steps: 1) obtaining a nucleic acid sample from a patient; and ii) detecting in the sample the identity of nucleotide or nucleotides at one or more polymorphic nucleotide positions listed in Tables 1-1 (SEQ ID NO: 1-8) and 2-1 (SEQ ID NO: 9).

In an additional aspect, methods of identifying a modulator of a PD phenotype are also provided. The methods include contacting a potential modulator to a gene or gene product, e.g. wherein the gene or gene product comprises or is closely linked to a polymorphism described herein (e.g. in Table 1-1 (SEQ ID NO: 1-8) and/or Table 2-1 (SEQ ID NO: 9)). An effect of the potential modulator on the gene or gene product is detected, thereby identifying whether the potential modulator modulates the phenotype.

Kits for performing any of the methods herein are another feature of the disclosure in this application. Such kits can include probes or amplicons for detecting any polymorphism herein, appropriate packaging materials, and instructions for practicing the methods.

The application also provides systems for generating a prognosis of a human subject's increased or decreased susceptibility to PD based on genotyping data spanning hundreds of thousands of single nucleotide polymorphisms. The system may include means for storing a subject's profile comprising a set of patient-specific information including subject's medical history, family medical history and subject's genetic testing results including genotypes at the various polymorphic sites listed in Tables 1-1 (SEQ ID NO: 1-8) and 2-1 (SEQ ID NO: 9).

The invention also provides methods of PD prognosis based on expression profiling. Such methods include determining the expression levels of at least 2 and no more than 5,000 genes in a subject, wherein at least two of the genes are selected from the group consisting of MCCC1, TMEM175, RIT2, GAK, DGKQ, RIN, SYT4, STBD1, SCARB2, HLA-DRB1, HLA-DQA1, LOC729862, PGDB3P2 and LRKK2, wherein the expression levels are used to create an expression profile. In one aspect the expression levels are used for PD prognosis by comparing expression levels of the genes in a human subject to expression levels of the genes in a control subject known to have Parkinson's disease (PD) and/or a healthy control subject known to not have PD, wherein similarity of expression profiles in the subject and the control subject having PD is suggestive the subject has a higher likelihood of having or developing Parkinson's disease, and similarity of the expression profiles of the subject and a control subject not having PD—is suggestive the subject has a lower likelihood of having or developing Parkinson's disease.

Any of the above methods can include informing the patient or a relative thereof of the presence of or susceptibility to PD; or further comprising administering a treatment regimen effective to treat or effect prophylaxis of PD.

DEFINITIONS

Terms and symbols of genetics, molecular biology, biochemistry and nucleic acid used herein follow those of standard treatises and texts in the field, e.g. Kornberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

All terms are to be understood with their typical meanings established in the relevant art. Without limiting any term, further clarifications for some of the terms are provided below:

The term "nucleic acid" refers to a deoxyribonucleotide or ribonucleotide, whether singular or in polymers, naturally occurring or non-naturally occurring, double-stranded or single-stranded, coding (e.g. translated gene) or non-coding (e.g. regulatory region), or any fragments, derivatives, mimetics or complements thereof. Examples of nucleic acids include oligonucleotides, nucleotides, polynucleotides, nucleic acid sequences, genomic sequences, antisense nucleic acids, DNA regions, probes, primers, genes, regulatory regions, introns, exons, open-reading frames, binding sites, target nucleic acids and allele-specific nucleic acids. A nucleic acid can include one or more polymorphisms, variations or mutations (e.g., SNPs, insertions, deletions, inversions, translocations, etc.). A nucleic acid includes analogs (e.g., phosphorothioates, phosphoramidates, methyl phosphonate, chiral-methyl phosphonates, 2-O-methyl ribonucleotides) or modified nucleic acids (e.g., modified backbone residues or linkages) or nucleic acids that are combined with carbohydrates, lipids, protein or other materials, or peptide nucleic acids (PNAs) (e.g., chromatin, ribosomes, transcriptosomes, etc.) or nucleic acids in various structures (e.g., A DNA, B DNA, Z-form DNA, siRNA, tRNA, ribozymes, etc.). A nucleic acid may also include a detectable label. The term "detectable label" as used herein refers to, for example, a luminescent label, a light scattering label or a radioactive label, or any other form of labeling that can be detected by a physical, chemical, or a biological process. Fluorescent labels include commercially available fluorescein phosphoramidites such as Fluoreprime (Pharmacia), Fluoredite (Millipore) and FAM (ABI).

The term "hybridization" as used herein refers to the process in which two single-stranded polynucleotides bind non-covalently to form a stable double-stranded polynucleotide; triple-stranded hybridization is also theoretically possible. Hybridizations are usually performed under stringent conditions. For example, conditions of 5×SSPE (750 mM NaCl, 50 mM NaPhosphate, 5 mM EDTA, pH 7.4) and a temperature of 25-30° C. are suitable for allele-specific probe hybridizations. The term "specific hybridization" refers to the ability of a first nucleic acid to bind, duplex or hybridize to a second nucleic acid in a manner such that the second nucleic acid can be identified or distinguished from other components of a mixture (e.g., cellular extracts, genomic DNA, etc.). In certain embodiments, specific hybridization is performed under stringent conditions.

The term "hybridization-based assay" means any assay that relies on the formation of a stable duplex or triplex between a probe and a target nucleotide sequence for detecting or measuring such a sequence. Hybridization-based assays include, without limitation, assays based on use of oligonucleotides, such as polymerase chain reactions, oligonucleotide ligation reactions, single-base extensions of primers, circularizable probe reactions, allele-specific oligonucleotide hybridizations, either in solution phase or bound to solid phase supports, such as microarrays or microbeads.

The terms "isolated" and "purified" refer to a material that is substantially or essentially removed from or concentrated in its natural environment. For example, a purified nucleic acid is one that is separated from the nucleic acids that normally flank it or from other biological materials (e.g., other nucleic acids, proteins, lipids, cellular components, etc.) in a sample.

The term "linkage disequilibrium" refers to the preferential segregation of a particular polymorphic form with another polymorphic form at a different chromosomal location more frequently than expected by chance.

The term "modulate" refers to a change in expression, lifespan, function or activity of a nucleic acid or a protein. Such changes may include, for example, an increase, decrease, alteration, enhancement or inhibition of expression or activity of a nucleic acid or protein.

The term "PD-related nucleic acid" refers to a nucleic acid, or fragment, derivative (e.g., RNA), variant, polymorphism, or complement thereof, associated with resistance or susceptibility to PD including, for example, at least one or more PD-associated polymorphisms, genomic regions spanning 10 kb immediately upstream and 10 kb immediately downstream of a PD-associated polymorphism, coding and non-coding regions of an associated gene, and/or genomic regions spanning 10 kb immediately upstream and 10 kb immediately downstream of an associated gene, and nucleotide variants thereof.

The term "phenotype" is a trait or collection of traits that is/are observable in an individual or population. The trait can be quantitative (a quantitative trait, or QTL) or qualitative. For example, susceptibility to Parkinson's disease is a phenotype that can be identified according to the methods and compositions of the application described herein.

A "PD susceptibility phenotype" is a phenotype that displays a predisposition towards developing Parkinson's disease in an individual. A phenotype that displays a predisposition for PD, can, for example, show a higher likelihood that the disease will develop in an individual with the phenotype than in members of a relevant general population under a given set of environmental conditions (diet, physical activity regime, geographic location, etc.).

The terms "polymorphism", "polymorphic nucleotide", "polymorphic site" or "polymorphic nucleotide position" refer to a position in a nucleic acid that possesses the quality or character of occurring in several different forms. A nucleic acid may be naturally or non-naturally polymorphic, e.g., having one or more sequence differences (e.g., additions, deletions and/or substitutions) as compared to a reference sequence. A reference sequence may be based on publicly available information (e.g., the U.C. Santa Cruz Human Genome Browser Gateway (genome.ucsc.edu/cgi-bin/hg-Gateway) or the NCBI website (www.ncbi.nlm.nih.gov)) or may be determined by a practitioner of the present invention using methods well known in the art (e.g., by sequencing a reference nucleic acid). A nucleic acid polymorphism is characterized by two or more "alleles", or versions of the nucleic acid sequence. Typically, an allele of a polymorphism that is identical to a reference sequence is referred to as a "reference allele" and an allele of a polymorphism that is different from a reference sequence is referred to as an "alternate allele", or sometimes a "variant allele". As used herein, the term "major allele" refers to the more frequently occurring allele at a given polymorphic site, and "minor allele" refers to the less frequently occurring allele, as present in the general or study population. The term "risk allele" as used herein refers to an allele of a genetic polymorphism associated with an increased risk for PD. The term "protective allele" as used herein refers to the allele associated with a decreased risk for PD.

The term "single nucleotide polymorphism" or "SNP" refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site. Single nucleotide polymorphisms can also arise from a deletion of a nucleotide or an insertion of a nucleotide relative to a reference allele.

DETAILED DESCRIPTION OF THE INVENTION

Figure 1:
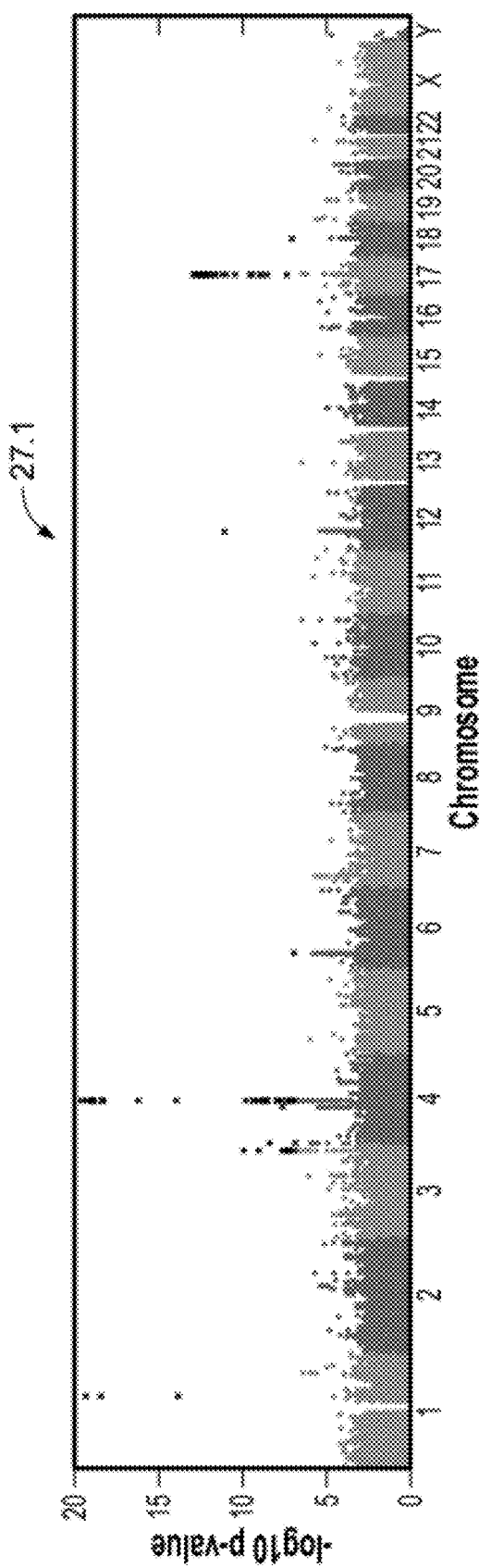
FIG. 1 depicts a Manhattan plot of the GWAS, showing the distribution of p-values along the genome, with chromosomes arranged along the X-axis, and all SNPs associated with p-values under 10e-7 represented with an "x".

The invention provides a set of novel polymorphisms associated with Parkinson's disease (PD). Identification of such polymorphisms is useful for the development and design of diagnostic or prognostic assays for PD. The polymorphisms may also have additional applications, including diagnostic and prognostic use in Parkinson's disease-related conditions, therapeutic treatments for Parkinson's disease, genetic linkage analysis and positional cloning.

I. Polymorphisms of the Invention

A genome-wide association study (GWAS) was performed to search for novel genetic variants associated with PD. Such studies have proven successful in identifying many hundreds of genetic associations to a wide range of diseases (Hirschhorn, J N (2009) *Genomewide Association Studies-Illuminating Biologic Pathways*, N Engl J Med 360: 1699-1701). Briefly, a GWAS is performed by collecting genome-wide SNP data on a large number of cases and controls and then testing each of the many (typically over 500,000) SNPs that were typed for significant frequency differences between cases and controls. A significant frequency difference is evidence that the SNP is associated with the disease, however due to the large multiple testing burden incurred by doing hundreds of thousands of tests, the association must be very significant to be considered true. Typical standards (employed by the applicants in the present application) require a p-value of under 1 e-7 and replication of the association in an independent sample.

The GWAS performed by the applicants identified a total of 12 SNPs independently and significantly associated with Parkinson's disease. Of these, 8 SNPs have never before been demonstrated to be associated with PD. In addition, 4 SNPs previously associated with PD replicated in the GWAS performed by the applicants. The presence of these 4 previously identified and well-known PD-associated SNPs in the set of significantly associated SNPs serves as supporting evidence for the validity of the study design and methodology. Finally, the GWAS performed by the applicants identified a novel PD-associated SNP modifying a known PD-associated mutation in the LRKK2 gene (LRRK2 G2019S, rs34637584).

Tables 1-1 (SEQ ID NO: 1-8) and 1-2 (SEQ ID NO: 1-8).

Tables 1-1 (SEQ ID NO: 1-8) and 1-2 (SEQ ID NO: 1-8) identify the 8 novel PD-associated SNPs that independently associated with PD. These SNPs were selected on the basis of fulfilling the following criteria: 1) a p-value under 1e-7 for association with PD; 2) replication in the National Institute of Neurological Disorders and Stroke (NINDS) Parkinson's disease dataset; 3) evidence of independent effect (significant after controlling for other SNPs in the list); and 4) no evidence of genotyping error.

SNP rs10513789 (SEQ ID NO: 1) is found in the following sequence:

```
SEQ ID NO: 1:
5'-tgatggtttttcaattttgttatgttgata[t/g]gtactgcatga taccagattacaaacaggg-3'.
```

The major allele is T, the minor allele is G, with the major allele being the risk allele. This association lies in an intron of MCCC1. Another candidate gene in this region is LAMP3, which has been found to be overexpressed in the brains of individuals with PD.

SNP rs6599389 (SEQ ID NO: 2) is found in the following sequence:

SEQ ID NO: 2:
5'-cccgccgtctctgtctcctcactccccgcc[g/a]tttgttgctgc ctcagcttctgttttcccc-3'.

The major allele is G, the minor allele is A, with the minor allele being the risk allele. This SNP lies in an intron of TMEM175. Other candidate genes in this region include GAK and DGKQ. GAK is a promising candidate gene as it is differentially expressed in Parkinson's disease in the substantia nigra (Grünblatt et al (2004) *Gene expression profiling of parkinsonian substantia nigra pars compacta: alterations in ubiquitin-proteasome, heat shock protein, iron and oxidative stress regulated proteins, cell adhesion/cellular matrix and vesicle trafficking genes*, J Neural Transm 111(12):1543-73).

SNP rs873785 (SEQ ID NO: 3) is found in the following sequence:

SEQ ID NO: 3:
5'-tcgtgatcccccttcgtctttcaacacctc[a/g]gtgtttctctt cccggtgaacatctactcg-3'.

The major allele is A, the minor allele is G, with the major allele being the risk allele. This SNP lies in an intron of GAK. Other candidate genes in this region include TMEM175 and DGKQ.

SNP rs11248060 (SEQ ID NO: 4) is found in the following sequence:

SEQ ID NO: 4:
5'-cttgtgggttcacacatagctgtgaggaaa[c/t]tgaacagaccc cctgaagcctttgtcagct-3'.

The major allele is C, the minor allele is T, with the minor allele being the risk allele. This SNP lies in an intron of DGKQ. Other candidate genes in this region include TMEM175 and GAK.

SNP rs4130047 (SEQ ID NO: 5) is found in the following sequence:

SEQ ID NO: 5:
5'-atcagaacgattctaggtgataatctttta[t/c]ggtcagagttt tcaaaaatggcagaaacat-3'.

The major allele is T, the minor allele is C, with the minor allele being the risk allele. SNP rs4130047 (SEQ ID NO: 5) lies near two possible candidate genes. The first candidate gene, RIT2, contains rs4130047 (SEQ ID NO: 5) in an intron. RIT2 is similar to RIN, a gene potentially implicated in calcium-mediated signaling within neurons. Rin expression in brain is widespread but variable, with moderate expression in the majority of neurons throughout the diencephalon, midbrain, and hindbrain. The SNP is also close to SYT4 (synaptotagmin IV), which is expressed in the brain. SYT4 expression levels in brain are highest in the hippocampus, with substantial levels also detected in the amygdala and thalamus.

SNP rs6812193 (SEQ ID NO: 6) is found in the following sequence:

SEQ ID NO: 6:
5'-cctactaagttggggaaagctggatttgaa[c/t]cctggtctgtc aaaatccaaaggccatgtt-3'.

The major allele is C, the minor allele is T, with the major allele being the risk allele. SNP rs6812193 (SEQ ID NO: 6) lies in an intron of STBD1. Another candidate gene in this region is SCARB2, which binds to GBA in mice (Reczek D. et al (2007) *LIMP-2 Is a Receptor for Lysosomal Mannose-6-Phosphate-Independent Targeting of beta-Glucocerebrosidase*, Cell Nov 16; 131(4):770-83). GBA is known to be associated with PD (E. Sidransky (2009) *Multicenter Analysis of Glucocerebrosidase Mutations in Parkinson's Disease*, NEJM, Volume 361:1651-1661).

SNP rs7451962 (SEQ ID NO: 7) is found in the following sequence:

SEQ ID NO: 7:
5'-gcgctttatttctaggaagggcaggaattc[g/a]gaatccctcat cctgtcccagctacctgt-3'.

The major allele is G, the minor allele is A, with the minor allele being the risk allele. SNP rs7451962 (SEQ ID NO: 7) candidate genes include HLA-DRB1 and HLA-DQA1. This SNP helps to tag the HLA type DQA1*0102, which is a risk allele for multiple sclerosis.

SNP rs4397141 (SEQ ID NO: 8) is found in the following sequence:

SEQ ID NO: 8:
5'-attggtcttttatactgtattttaatata[c/t]cttttgtatgt ttagacatacagatcttta-3'.

The major allele C, the minor allele is T, with the major allele being the risk allele. The candidate genes include LOC729862, and PGBD3P2. LOC729862 is similar to Striatin, which is a protein involved in locomotor activity. Down regulation of striatin impairs the growth of dendrites as well as rat locomotor activity. (Castets et al. (2000) *Zinedin, SG2NA, and striatin are calmodulin-binding, WD repeat proteins principally expressed in the brain*. J. Biol. Chem. 275:19970-19977). PGBD3P2 is annotated as a pseudogene of a gene derived from a transposable element.

Tables 2-1 (SEQ ID NO: 9) and 2-2 (SEQ ID NO: 9).

Tables 2-1 (SEQ ID NO: 9) and 2-2 (SEQ ID NO: 9) identify a novel PD-associated SNP rs11755699 (SEQ ID NO: 9) that modifies a known PD-associated mutation in the LRRK2 gene (LRRK2 G2019S, rs34637584). Among people who carry the LRRK2 G2019S mutation, people with the minor allele C at rs11755699 (SEQ ID NO: 9) have a lower risk of developing Parkinson's disease.

SNP rs11755699 (SEQ ID NO: 9) is found in the following sequence:

SEQ ID NO: 9:
5'-tgtgtcacagattcaaagctcttcgttccc[t/c]gaagtcctgct actgtgacttggaactctc-3'.

The major allele is T, the minor allele is C, with the minor allele being the protective allele. SNP rs11755699 (SEQ ID NO: 9) lies in an intron of SGK1, a gene known to be associated with cell survival in neurodegenerative disease (Stichel et al. (2005) *Sgk1, a member of an RNA cluster associated with cell death in a model of Parkinson's disease*, Eur J. Neurosci. 21(2):301-316; and Schoenebeck et al. (2005) *Sgk1, a cell survival response in neurodegenerative diseases*, Mol Cell Neurosci. 30(2):249-264).

Table 3.

Table 3 lists 4 SNPs previously associated with PD that replicated in the GWAS performed by the applicants. The 4 replicated SNPs met the same selection criteria as the 8 novel SNPs identified by the applicants in Tables 1-1 (SEQ ID NO: 1-8) and 1-2 (SEQ ID NO: 1-8), and serve as supporting evidence for the validity of the study design and methodology.

It is to be understood that Tables 1-1 (SEQ ID NO: 1-8) and 2-1 (SEQ ID NO: 9) provide only a partial list of candidate genes associated with the novel PD-associated SNPs identified herein. Other candidate genes or genomic regions, include, for example, sequences spanning 10 kb immediately upstream and 10 kb immediately downstream of a PD-associated SNP, coding and non-coding regions of an associated gene, and/or genomic regions spanning 10 kb immediately upstream and 10 kb immediately downstream of an associated gene, and nucleotide variants thereof.

TABLE 1-2

Novel PD-associated SNPs.

| SNP ID | Sequence (+) |
|---|---|
| rs10513789 (SEQ ID NO: 1) | TGATGGTTTTTCAATTTTGTTATGTTGATA [T/G]GTACTGCATGATACCAGATTACAAACAGGG |
| rs6599389 (SEQ ID NO: 2) | CCCGCCGTCTCTGTCTCCTCACTCCCCGCC [G/A]TTTGTTGCTGCCTCAGCTTCTGTTTTCCCC |
| rs873785 (SEQ ID NO: 3) | TCGTGATCCCCCTTCGTCTTTCAACACCTC [A/G]TGTTTCTCTTCCCGGTGAACATCTACTCG |
| rs11248060 (SEQ ID NO: 4) | CTTGTGGGTTCACACATAGCTGTGAGGAAA [C/T]TGAACAGACCCCCTGAAGCCTTTGTCAGCT |
| rs4130047 (SEQ ID NO: 5) | ATCAGAACGATTCTAGGTGATAATCTTTTA [T/C]GGTCAGAGTTTTCAAAAATGGCAGAAACAT |
| rs6812193 (SEQ ID NO: 6) | CCTACTAAGTTGGGGAAAGCTGGATTTGAA [C/T]CCTGGTCTGTCAAAATCCAAAGGCCATGTT |
| rs7451962 (SEQ ID NO: 7) | GCGCTTTATTTCTAGGAAGGGCAGGAATTC [G/A]GAATCCCTCATCCTGTCCCCAGCTACCTGT |

TABLE 1-1

Novel PD-associated SNPs.

| SNP ID | Chromosome | Locus | Other candidate genes | Position | Alleles | MAF | Score | OR | 95% CI |
|---|---|---|---|---|---|---|---|---|---|
| rs10513789 (SEQ ID NO: 1) | 3 | MCC1 | LAMP3 | 184.242.767 | T/G | 0.2 | 9.27 | 0.801 | [0.75-0.86] |
| rs6599389 (SEQ ID NO: 2) | 4 | TMEM175 | GAK, DGKQ | 929.113 | G/A | 0.073 | 7.41 | 1.316 | [1.20-1.45] |
| rs873785 (SEQ ID NO: 3) | 4 | GAK | TMEM175, DGKQ | 915.149 | A/G | 0.37 | 7.78 | 0.847 | [0.80-0.90] |
| rs11248060 (SEQ ID NO: 4) | 4 | DGKQ | TMEM175, GAK | 954.359 | C/T | 0.13 | 7.10 | 1.220 | [1.13-1.32] |
| rs4130047 (SEQ ID NO: 5) | 18 | RIT2 | SYT4 | 38.932.233 | T/C | 0.31 | 7.59 | 1.178 | [1.11-1.25] |
| rs6812193 (SEQ ID NO: 6) | 4 | STBD1 | SCARB2 | 77.418.010 | C/T | 0.36 | 7.48 | 0.857 | [0.81-0.91] |
| rs7451962 (SEQ ID NO: 7) | 6 | HLA-DRB1 | HLA-DQA1 | 32.690.413 | G/A | 0.442 | 6.937 | 1.15 | [1.1-1.2] |
| rs4397141 (SEQ ID NO: 8) | 5 | LOC729862 | PGBD3P2 | 29.647.646 | C/T | 0.0797 | 5.998 | 0.77 | [0.69-0.86] |

The SNPs listed in the table independently and significantly associated with Parkinson's disease. Position refers to NCBI Build 36. Alleles refer to major/minor alleles on forward strand, with the risk allele identified in bold. The major/minor allele order is based on allelic frequencies in the study cohort.
MAF = minor allele frequency,
Score = P-value of association test at $-\log_{10}$ p-value,
OR = odds ratio per copy of the minor allele,
CI = confidence interval.
Odds ratio >1 means the minor allele is associated with Parkinson's disease.

TABLE 1-2-continued

Novel PD-associated SNPs.

| SNP ID | Sequence (+) |
|---|---|
| rs4397141 (SEQ ID NO: 8) | ATTGGTCTTTTATACTGTATTTTTAATATA[C/T]CTTTTGTATGTTTAGACATACAGATCTTTA |

Sequences are shown in the forward reference strand, with the risk allele identified in bold.

TABLE 2-1

Novel PD-associated SNP rs111755699.

| SNP ID | Chromosome | Locus | Other candidate genes | Position | Alleles | MAF | Score | OR | 95% CI |
|---|---|---|---|---|---|---|---|---|---|
| rs11755699 (SEQ ID NO: 9) | 6 | SGK1 | — | 134.640.940 | T/C | 0.0639 | 2.57 | 5.677 | [1.67-19.27] |

The SNP rs111755699 modifies a known PD-associated mutation in the LRKK2 gene. Position refers to NCBI Build 36. Alleles refer to major/minor alleles on forward strand, with the protective allele identified in bold. The major/minor allele order is based on allelic frequencies in the study cohort.
MAF = Minor allele frequency,
Score = P-value of association test at $-\text{Log}_{10}$ p-value,
OR = odds ratio per copy of the minor allele,
CI = confidence interval.
Odds ratio >1 means the minor allele is associated with Parkinson's disease.

TABLE 2-2

Novel PD-associated SNP rs111755699.

| SNP ID | Sequence (+) |
|---|---|
| rs11755699 (SEQ ID NO: 9) | TGTGTCACAGATTCAAAGCTCTTCGTTCCC[T/C]GAAGTCCTGCTACTGTGACTTGGAACTCTC |

Sequence is shown in the forward reference strand, with the protective allele identified in bold.

TABLE 3

SNPs previously associated with PD which replicated in the GWAS performed by the applicants.

| SNP ID | Chromosome | Locus | Position | Alleles | MAF | Score | OR | 95% CI |
|---|---|---|---|---|---|---|---|---|
| rs3467584 | 12 | LRRK2 | 39.020.459 | G/A | 0.0029 | 20.81 | 5.788 | [3.96-8.46] |
| GBA N370S | 1 | GBA | 153.472.258 | T/C | 0.0052 | 19.75 | 3.657 | [2.77-4.83] |
| rs356220 | 4 | SNCA | 90.860.363 | C/T | 0.38 | 18.94 | 1.293 | [1.22-1.37] |
| rs2316765 | 17 | MAPT | 41.268.235 | T/C | 0.21 | 11.50 | 0.777 | [0.72-0.83] |

Position refers to NCBI Build 36. Alleles refer to major/minor alleles on forward strand. The major/minor allele order is based on allelic frequencies in the study cohort.
MAF = Minor allele frequency,
Score = P-value of association test at $-\text{Log}_{10}$ p-value,
OR = odds ratio per copy of the minor allele,
CI = confidence interval.
Odds ratio >1 means the minor allele is associated with Parkinson's disease.

II. Methods of Use of Polymorphisms of the Invention

The present invention provides, in part, novel methods for identifying individuals at an increased risk for PD. The SNPs, alleles and associated genes and genomic regions identified in Tables 1-1 (SEQ ID NO: 1-8) and 2-1 (SEQ ID NO: 9) can be used to identify, isolate and amplify PD-related nucleic acids. Such nucleic acids can be useful for prognostics, diagnostics, prevention, treatment and further study of PD.

In one embodiment, the nucleic acids identified in Tables 1-2 (SEQ ID NO: 1-8) and 2-2 (SEQ ID NO: 9) can specifically hybridize to genomic regions associated with PD. Due to the duplex nature of DNA, it will be clear to one skilled in the art that sequence complementary to those provided in Tables 1-2 (SEQ ID NO: 1-8) to 2-2 (SEQ ID NO: 9) can also specifically hybridize to the genomic regions associated with PD, and are contemplated to be part of the instant invention. Nucleic acids provided in Tables 1-2 (SEQ ID NO: 1-8) and 2-2 (SEQ ID NO: 9) and their complementary sequences can, in some embodiments, specifically hybridize to a genomic sequence containing the polymorphisms identified in Tables 1-1 (SEQ ID NO: 1-8) to 2-1 (SEQ ID NO: 9).

In a preferred embodiment, the nucleic acids identified herein and those in linkage disequilibrium with them, are associated with an increased or decreased risk for PD. The nucleic acids in linkage disequilibrium with those disclosed herein usually occur in the same genes or with 100 kb of the same genes. A nucleic acid associated with increased risk for PD is one that contains the risk allele at the polymorphisms identified at Tables 1-1 (SEQ ID NO: 1-8) and 2-1 (SEQ ID NO: 9). A nucleic acid associated with decreased risk for PD is one that contains the protective allele at the polymorphisms identified at Tables 1-1 (SEQ ID NO: 1-8) and 2-1 (SEQ ID NO: 9).

Conditions for nucleic acid hybridization vary depending on the buffers used, length of nucleic acids, ionic strength, temperature, etc. The term "stringent conditions" for hybridization refers to the incubation and wash conditions (e.g., conditions of temperature and buffer concentration) that permit hybridization of a first nucleic acid to a second nucleic acid. The first nucleic acid may be perfectly (e.g. 100%) complementary to the second or may share some degree of complementarity, which is less than perfect (e.g., more than 70%, 75%, 85%, or 95%). For example, certain high stringency conditions can be used which distinguish perfectly complementary nucleic acids from those less complementary, even those having only a single base mismatch. High stringency, moderate stringency and low stringency conditions for nucleic acid hybridization are known in the art. Ausubel, F. M. et al., *Current Protocols in Molecular Biology* (John Wiley & Sons 1998), pages 2.10.1-2.10.16; 6.3.1-6.3.6. The exact conditions which determine the stringency of hybridization depend not only on ionic strength (e.g., 0.2.times.SSC, 0.1.times.SSC), temperature (e.g., room temperature, 42 C, 68 C) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Equivalent conditions can be determined by varying one or more of these parameters while maintaining a similar degree of identity or similarity between the two nucleic acid molecules.

Probes and Primers.

The nucleic acids herein can be used as probes and primers in various assays. The terms "probe" and "primer" refer to nucleic acids that hybridize, in whole or in part, in a sequence-specific manner to a complementary strand. Probes with a detectable label can be used in cloning of full-length cDNA or genomic DNA by screening cDNA or genomic DNA libraries.

In certain embodiments, the term "primer" refers to a single-stranded nucleic acid that can act as a point of initiation of template-directed DNA synthesis, such as in PCR. PCR reactions can be designed based on the human genome sequence and the associated genomic regions or polymorphisms. For example, where a polymorphism is located in an exon, the exon can be isolated and amplified using primers that are complementary to the nucleotide sequences at both ends of the exon. Similarly, where a polymorphism is located in an intron, the entire intron can be isolated and amplified using primers that are complementary to the nucleotide sequences at both ends of the intron.

In preferred embodiments, a probe or primer contains a region of at least about 10 contiguous nucleotides, preferably at least about 16 contiguous nucleotides, more preferably about 20 or about 30 or about 50 contiguous nucleotides, that can specifically hybridize to a complementary nucleic acid sequence. In addition, a probe or primer is preferably about 100 or fewer nucleotides, more preferably between 6 and 50 nucleotides, and more preferably between 12 and 30 nucleotides in length. In certain embodiments, a first portion of a probe or primer is perfectly complementary to a target nucleic acid, and a second portion of the probe or primer is not perfectly complementary to the target nucleic acid. In some aspects, the portion that is not perfectly complementary contains a binding site, e.g., for a polypeptide or another probe or primer.

Detection of PD-Related Nucleic Acids.

Detection of the presence or increased level of one or more nucleic acids, or fragments, derivatives, polymorphisms, variants or complements thereof, associated with resistance or susceptibility to PD-related disease can be used as a prognostic and diagnostic tool for PD.

In some aspects of the present application, a gene or a genomic region comprising or under the control of a PD-related nucleic acid may be differentially expressed. "Differential expression" as used herein refers to both quantitative and qualitative differences in a gene's expression patterns including, e.g., changes in tissue-specificity or temporal aspects of expression. Detection of such expression patterns may be made by standard techniques well known to those of skill in the art, for example, differential screening (Tedder et al. (1998) Proc. Natl. Acad. Sci. USA 85:208-212), subtractive hybridization (Hedrick et al. (1984) Nature 308:149-153; Lee et al. (1984) Proc. Natl. Acad. Sci. USA 88:2825), differential display (Liang et al., U.S. Pat. No. 5,262,311), reverse transcriptase-(RT-) PCR and/or Northern analysis.

In other aspect of the present application, a gene comprising, or under the control of a PD-related nucleic acid may exhibit differential allelic expression. "Differential allelic expression" as used herein refers to both qualitative and quantitative differences in the allelic expression of multiple alleles of a single gene present in a cell. As such, a gene displaying differential allelic expression may have one allele expressed at a different time or level as compared to a second allele in the same cell/tissue. Differential allelic expression and analysis methods therefore are disclosed in detail in U.S. patent application Ser. No. 10/438,184, filed May 13, 2003 and U.S. patent application Ser. No. 10/845,316, filed May 12, 2004, incorporated into this application in its entirety herein.

Detection of nucleic acids may be made using any method known in the art, for example, Southern or northern analyses, in situ hybridization analyses, single-stranded conformational polymorphism analyses, polymerase chain reaction analyses and nucleic acid microarray analyses, all of which are well known to those of skill in the art. Such analyses may reveal not only the alleles present in a test sample, but also both quantitative and qualitative aspects of the expression pattern of polypeptides encoded by PD-related nucleic acids. In particular, such analyses may reveal expression patterns of polypeptides associated with resistance or susceptibility to PD-related disease.

In one example, a diagnosis or prognosis is made using a test sample containing genomic DNA or RNA obtained from an individual to be tested. The individual can be an adult, child or fetus. In a preferred embodiment, the individual is a human. The test sample can be from any source which contains genomic DNA or RNA, including for example, blood, amniotic fluid, cerebrospinal fluid, skin, muscle, buccal or conjunctival mucosa, placenta, gastrointestinal tract or other tissues. In a preferred embodiment a DNA or RNA sample is obtained from neuronal tissue. Alternatively, a test sample of DNA from fetal cells or tissue can be obtained by appropriate methods such as by amniocentesis or chorionic villus sampling. The test sample is subjected to one or more tests to identify the presence or absence of a nucleic acid of interest (e.g., a PD-related nucleic acid).

In one embodiment, the test sample is subjected to purification, isolation and/or amplification techniques, many of which are well known in the art (e.g., Sambrook et al. (1989) Molecular Cloning, A Laboratory Manual, Cold Spring Harbor Press, N.Y.; and Ausubel et al. (eds. 1987-1993), Current Protocols in Molecular Biology, John Wiley & Sons, Inc. New York).

In one embodiment, Southern blot, northern blot or similar analyses methods are used to identify the presence or absence of one or more genomic DNA sequences associated with resistance or susceptibility to PD using complementary nucleic acid probes. In certain embodiments, the nucleic acid probes are labeled before they are contacted with the test sample; in other embodiments, the nucleic acids in the test sample are labeled before they are contacted with the nucleic acid probes.

Alternative diagnostic and prognostic methods employ amplification of target nucleic acids associated with resistance or susceptibility to PD, e.g., by PCR. This is especially useful for target nucleic acids present in very low quantities. In one embodiment, amplification of target nucleic acids associated with resistance to PD indicates their presence and is a prognostic and diagnostic of resistance to PD. In a related embodiment, amplification of target nucleic acids associated with susceptibility to PD indicates their presence and is a prognostic and diagnostic of susceptibility to PD.

Microarrays can also be utilized for diagnosis and prognosis of resistance or susceptibility to PD-related disease. Microarrays comprise probes that are complementary to target nucleic acid sequences from an individual. A microarray probe is preferably allele-specific. In one embodiment, the microarray comprises a plurality of different probes, each coupled to a surface of a substrate in different known locations and each, capable of binding complementary strands. See, e.g. U.S. Pat. No. 5,143,854 and PCT Publication Nos. WO 90/15070 and WO 92/10092. These microarrays can generally be produced using mechanical synthesis methods or light-directed synthesis methods that incorporate a combination of photolithographic methods and solid phase oligonucleotide synthesis methods. See Fodor et al., (1991) Science 251:767-777; and U.S. Pat. No. 5,424,186. Techniques for the mechanical synthesis of microarrays are described in, for example, U.S. Pat. No. 5,384,261.

Other methods to detect polymorphic nucleic acids include, for example, direct manual sequencing (Church and Gilbert, (1988) Proc. Natl. Acad. Sci. USA 81:1991-1995; Sanger, F. et al. (1977) Proc. Natl. Acad. Sci. USA 74:5463-5467; and U.S. Pat. No. 5,288,644); automated fluorescent sequencing; single-stranded conformation polymorphism assays; clamped denaturing gel electrophoresis; denaturing gradient gel electrophoresis (Sheffield, V. C. et al. (1981) Proc. Natl. Acad. Sci. USA 86:232-236), mobility shift analysis (Orita, M. et al. (1989) Proc. Natl. Acad. Sci. USA 86:2766-2770), restriction enzyme analysis (Flavell et al. (1978) Cell 15:25; Geever, et al. (1981) Proc. Natl. Acad. Sci. USA 78:5081); heteroduplex analysis; Tm-shift genotyping (Germer et al. (1999) Genome Research 9:72-78); kinetic PCR (Germer et al. (2000) Genome Research 10:258-266); chemical mismatch cleavage (Cotton et al. (1985) Proc. Natl. Acad. Sci. USA 85:4397-4401); RNase protection assays (Myers, R. M. et al. (1985) Science 230:1242); and use of polypeptides which recognize nucleotide mismatches, such as *E. coli* mutS protein.

The invention also provides methods of expression profiling by determining levels of expression profiling of one or more genes of the invention, i.e. MCCC1, TMEM175, RIT2, GAK, DGKQ, RIN, SYT4, STBD1, SCARB2, HLA-DRB1, HLA-DQA1, LOC729862, PGDB3P and LRKK2. The methods preferably determine expression levels of at least 2, 5, or 10 or all of the above genes. Optionally, expression levels of other genes beyond those shown to be associated with PD in the present application are also determined. The polymorphisms listed in Tables 1-2 (SEQ ID NO: 1-8) and 2-2 (SEQ ID NO: 9) may have an effect on the expression profile of several other genes.

See http://www.plosgenetics.org/article/info:doi/10.1371/journal.pgen.1000888

PD Prognosis by Expression Profiling

The expression levels of one or more genes in discrete sample (e.g. from a particular individual or cell line) are referred to as an expression profile. Typically, the expression profile is compared with an expression profile of the same genes in a control sample. The control sample can be a negative control (e.g., an individual (or population of individuals) not having or susceptible to PD or a positive control (e.g., an individual (or population of individuals) having or susceptible to PD. The controls can be contemporaneous or historical. Individual expression levels in both the test and control samples can be normalized before comparison, e.g., by reference to the levels of a house keeping genes to avoid differences unrelated to the disease. The relative similarity of the expression profile of a test individual to the negative and positive control expression profiles is a measure of the individual's resistance or susceptibility to PD. For example, if an expression profile is determined for seven genes of the invention, and the expression levels in the test subject are more similar to the positive control than the negative control for five of the genes, one can conclude that the test individual has or is susceptible to PD or PD-related disorder. The analysis can be performed at a more sophisticated level by weighting expression level according to where they lie between negative and positive controls. For example, if there is a large difference between negative and positive controls, and an expression level of a particular gene in a test individual lies close to the positive control that expression level is accorded greater weight than an expression level in a gene in which there is a smaller difference in expression levels between negative and positive controls, and the expression level of the test individual lies only slightly above the midpoint of the negative and positive control expression levels.

Systems for Prognosis of PD

Systems for correlating the presence or absence of an allele with an increased or decreased susceptibility to PD are another aspect of the invention. The system will include instructions to compare detected information as to allele sequence with a database that includes correlations between the alleles and the incidence of PD. In another aspect, the system will also include a database containing allelic information for control subjects that have PD, and control subjects that do not have PD. A typical system will further include a database comprising detailed phenotypic information for a subject, medical history of the subject, family medical history and other lifestyle specific information for the subject. The system will also include a set of instructions to analyze the subject's risk of developing PD or identify the presence of PD in the subject based on the genetic profile of the subject and other measurable characteristics as stated above. In another aspect, the system will include links to external databases to allow a user to communicate results of the diagnosis or prognosis to a medical practitioner for effecting suitable treatment for the subject.

Screening for Small Molecules.

Agents that modulate the expression, function and/or activity of PD-related disease nucleic acids or polypeptides can be obtained using any of the numerous approaches in combinatorial library methods known in the art, including: biological libraries; natural products libraries; spatially addressable parallel solid phase or solution phase libraries; synthetic library methods requiring deconvolution; the 'one-bead one-compound' library method; and synthetic library methods using affinity chromatography selection. The biological library approach is largely limited to polypeptide libraries, while the other four approaches are applicable to polypeptide, non-peptide oligomer or small molecule libraries of compounds. See Lam, K. S. (1997) Anticancer Drug Des. 12:145.

Non-peptide agents or small molecules are generally preferred because they are more readily absorbed after oral administration and have fewer potential antigenic determinants. Small molecules are also more likely to cross the blood brain barrier than larger protein-based pharmaceuticals.

Methods for screening small molecule libraries for candidate protein-binding molecules are well known in the art and may be employed to identify molecules that modulate (e.g., through direct or indirect interaction) one or more of the PD-related disease polypeptides herein. Briefly, PD-related disease polypeptides may be immobilized on a substrate and a solution including the small molecules is contacted with the PD-related disease polypeptide under conditions that are permissive for binding. The substrate is then washed with a solution that substantially reflects physiological conditions to remove unbound or weakly bound small molecules. A second wash may then elute those compounds that are bound strongly to the immobilized polypeptide. Alternatively, the small molecules can be immobilized and a solution of PD-related disease polypeptides can be contacted with the column, filter or other substrate on which the small molecules are immobilized. The ability to detect binding of a PD-related disease polypeptide to a small molecule may be facilitated by labeling (e.g., radio-labeling or chemiluminescence) the polypeptide or small molecule.

Systems for screening modulators are also a feature of the application. The systems, genes linked to a polymorphism herein, or an encoded expression products of the gene. can include, e.g. The systems will typically include a detector that measures increased or decreased expression of the gene or gene product in the presence of the modulator; increased or decreased activity of the gene product in the presence of the modulator; or an altered expression pattern of the gene or gene product in the presence of the modulator. The systems can also include fluid handling elements for mixing and aliquotting modulator and/or the gene or product, mixing them, performing laboratory operations (e.g., purification, synthesis, cell culture, etc.). System instructions for recording modulator effects and, optionally, for selecting modulators are also an optional feature of these systems.

III. Examples

Study Design and Statistical Analysis

A. Cohort. The subjects with Parkinson's disease were recruited via a series of emails to the mailing lists of Parkinson's disease foundations and clinics. Emails were sent to all patients who had registered with these foundations as PD patients. A limited number of patients were also recruited in person at PD workshops and conferences. All patients were offered the 23andMe Personal Genome Service for $25. Over 75% of enrollees filled out an initial web-based survey that asked detailed questions about diagnosis and symptoms. The criteria for selection were that they were diagnosed with PD by a doctor and did not later change diagnosis. Most cases fit the clinical definitions of PD, including unilateral, gradual onset and response to dopaminurgic therapy. Controls were taken from the 23andMe customer database. All customers who did not say they were affected with PD were used as controls. This is reasonable since the prevalence of PD is under 2% in the general population, well under the typical misdiagnosis rate for PD. The final dataset included 3227 cases and 30,817 controls. The replication group consisted of 939 Parkinson's disease cases and 802 controls collected by NINDS and downloaded from dbGaP (http://www.ncbi.nlm.nih.gov/projects/gap/cgi-bin/study.cgi?study_id=phs000089.v3.p2).

B. Genotyping and SNP Quality Control. Samples were genotyped on the Illumina HumanHap550+ BeadChip platform (Illumina, Inc., San Diego, Calif. 92121), which included SNPs from the standard HumanHap550 panel in addition to a custom set of about 25,000 SNPs. A total of 609695 SNPs were genotyped on the 550+ plus custom platform. After quality control a total of 554197 SNPs were used in the analysis.

DNA extraction and genotyping were performed on saliva samples by National Genetics Institute (NGI, Los Angeles, Calif. 90064), a CLIA licensed clinical laboratory and a subsidiary of Laboratory Corporation of America. Every sample that failed to reach 98.5% call rate was re-analyzed. Individuals whose analyses failed repeatedly were re-contacted to provide additional samples. SNPs with a call rate under 98% were excluded from analysis, as were those with minor allele frequency under 0.5% or a p-value for Hardy-Weinberg equilibrium under 1e-10. Both minor allele frequency and Hardy-Weinberg statistics were calculated within the dataset. Due to the two slightly different platforms in the analysis the no-call rate was calculated only among individuals genotyped on a given platform. In addition, a total of 1553 SNPs with Mendelian discordance rates (the fraction of trios in which the called SNPs followed an impossible inheritance pattern) of at least 1% were discarded. Since cases and controls for this study were run in different batches, about 1000 additional SNPs were discarded due to the possibility of batch effects.

C. Statistical Methods. All p-values were calculated using logistic regression using the formula PD status~Genotype at SNP i+Sex+Age+PC1+PC2+PC3+PC4+PC5. Phenotype was coded as 1=PD patient, 0=unaffected. Genotypes were coded as 0, 1, and 2, counting the number of minor alleles present. Sex was coded as female=1, male=0. PC1 through PC5 are the first five principle components of genetic variation among all subjects. The reported odds ratio (OR) for each SNP is thus the odds per copy of the minor allele of that SNP present. The log of the odds ratio is the coefficient of the genotype in the above regression. For each novel association, the set of nearby SNPs was evaluated (FIGS. 3-6). In each case, the presence of signal in other nearby SNPs provides substantial evidence that these associations are not due to genotyping error.

D. Population Structure. Identity by descent (IBD) was measured for all pairs of participants using a novel algorithm, described in detail in pending application titled "Finding Relatives In a Database", application Ser. No. 12/644,791, and incorporated by reference into this application in its entirety herein. The aforementioned novel algorithm acts on unphased data by comparing homozygous calls in a window. A set of "unrelated" participants was defined by requiring that no two individuals share over 700 cM IBD, counting both full (diploid) and half (haploid) levels of identity by descent. This level of relatedness (approximately 20% of the genome) corresponds approximately to the minimal expected sharing between first-cousins in an outbred population. Only unrelated (in the aforementioned sense) individuals from this subset were considered during the present analysis.

Figure 2:
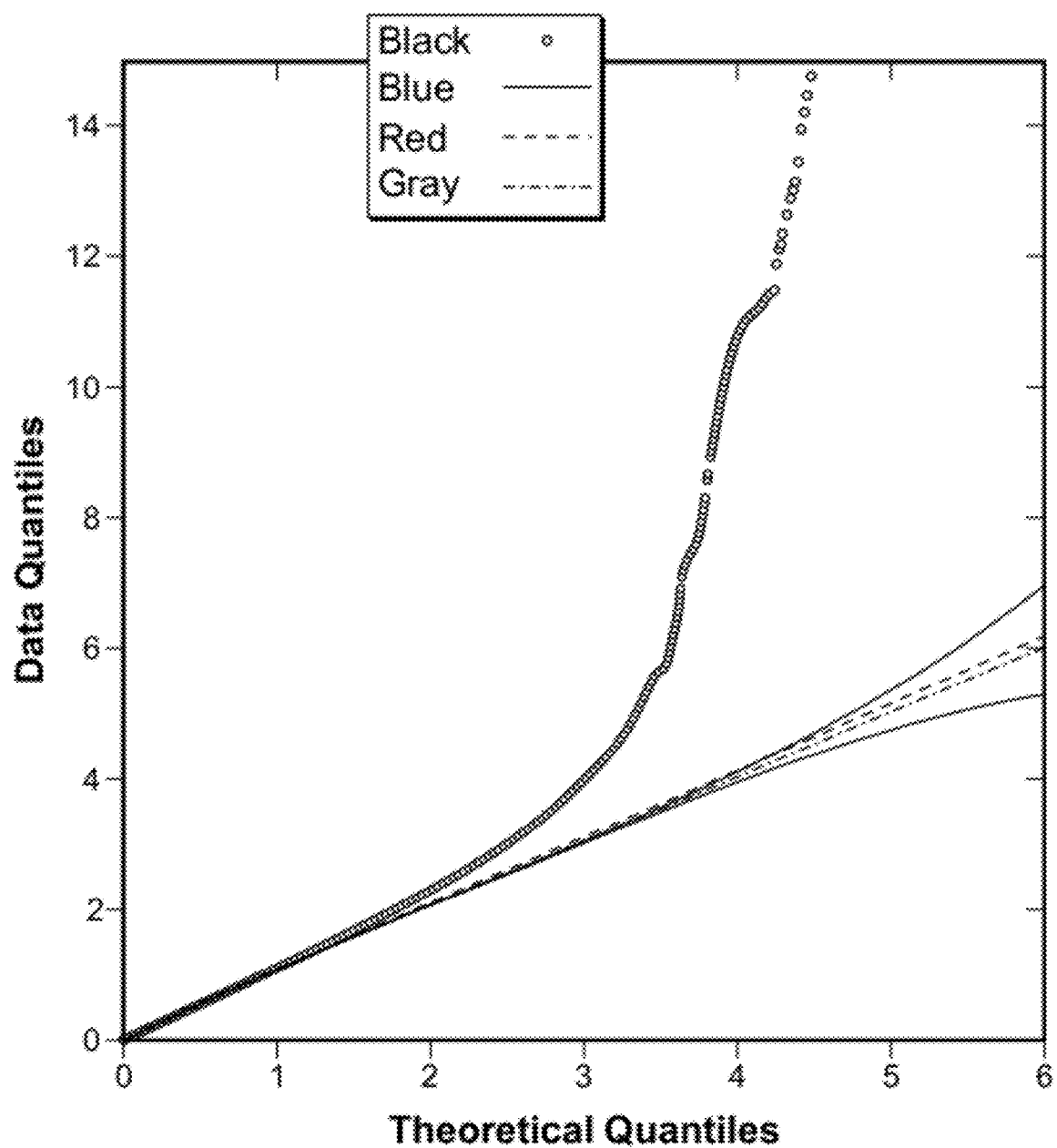
FIG. 2 depicts a quantile-quantile plot of the GWAS performed by the applicants. There is no evidence of population structure biasing the results, as the plot shows no inflation. The genomic inflation factor (Devlin and Roeder (1999) *Genomic control for association studies, Biometrics* 55:997-1004) was calculated to be 1.11.
Figure 3:
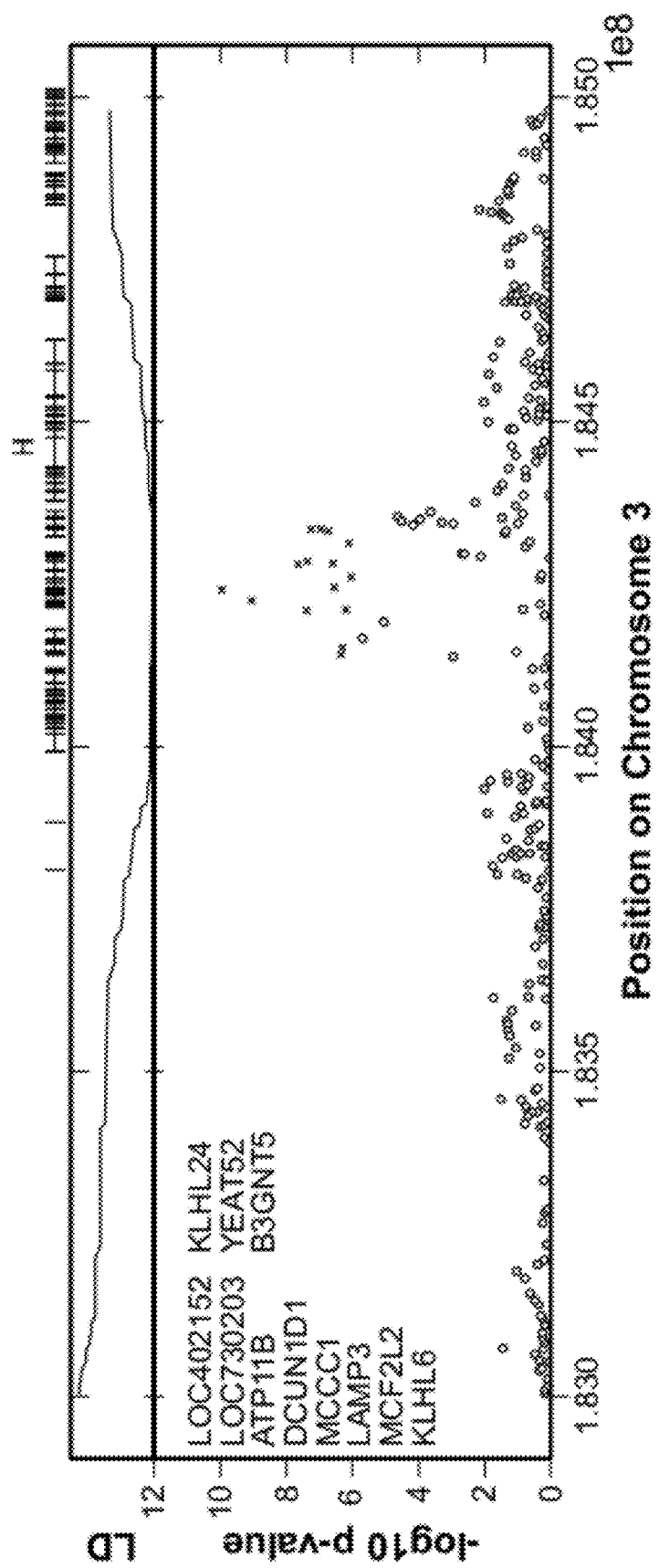
FIG. 3 depicts plots of the p-values surrounding significant SNPs around the MCCC1/LAMP3 region. SNPs with a p-value under 10e-6 are shown.
Figure 4:
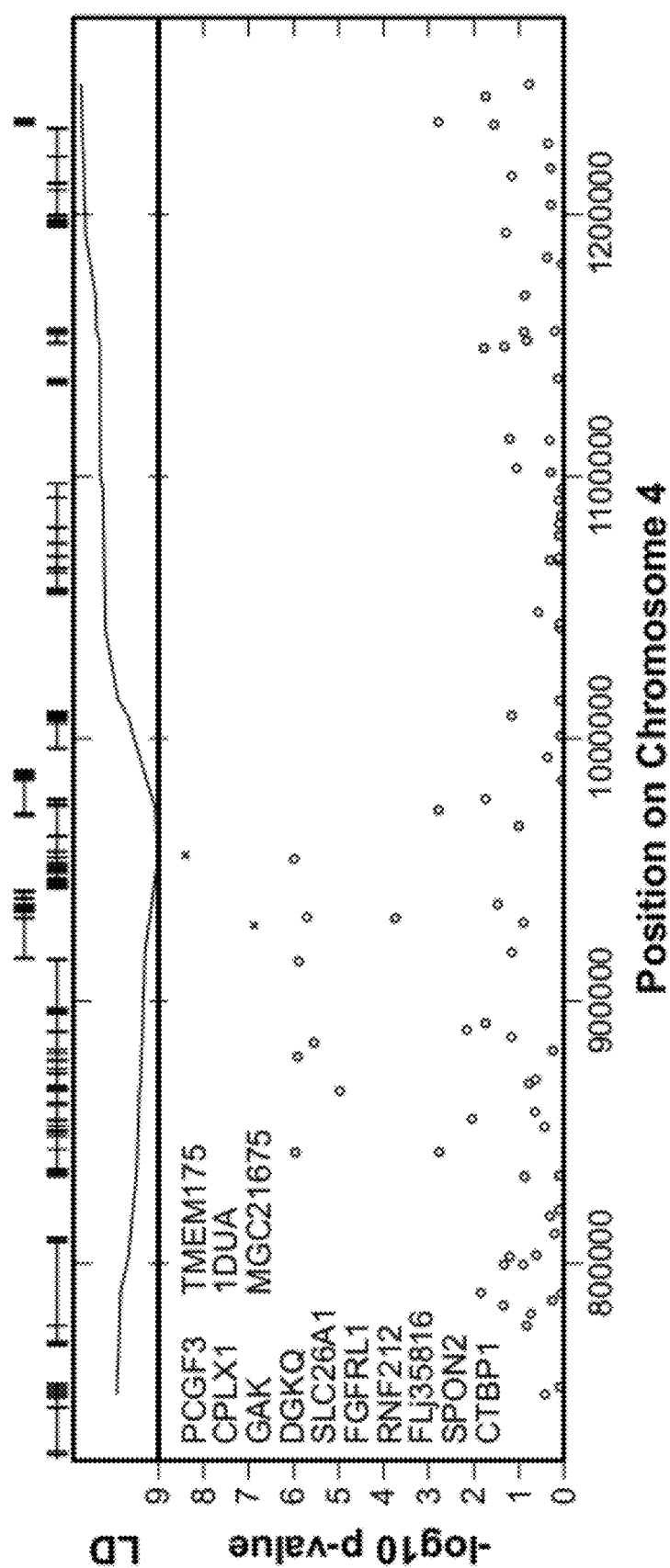
FIG. 4 depicts plots of the p-values surrounding significant SNPs around the GAK/DGKQ/TMEM175 region. SNPs with a p-value under 10 e-6 are shown.
Figure 5:
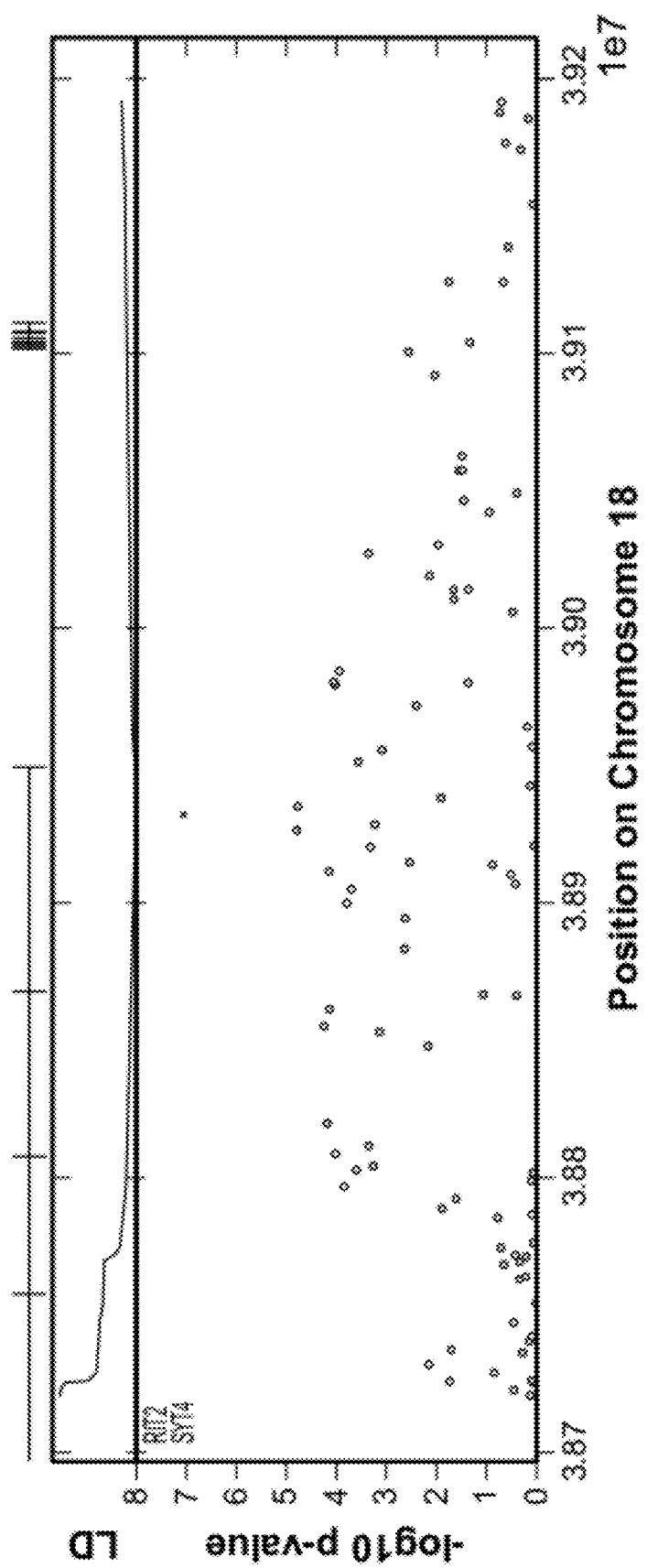
FIG. 5 depicts plots of the p-values surrounding significant SNPs around the RIT2 region. SNPs with a p-value under 10 e-6 are shown.
Figure 6:
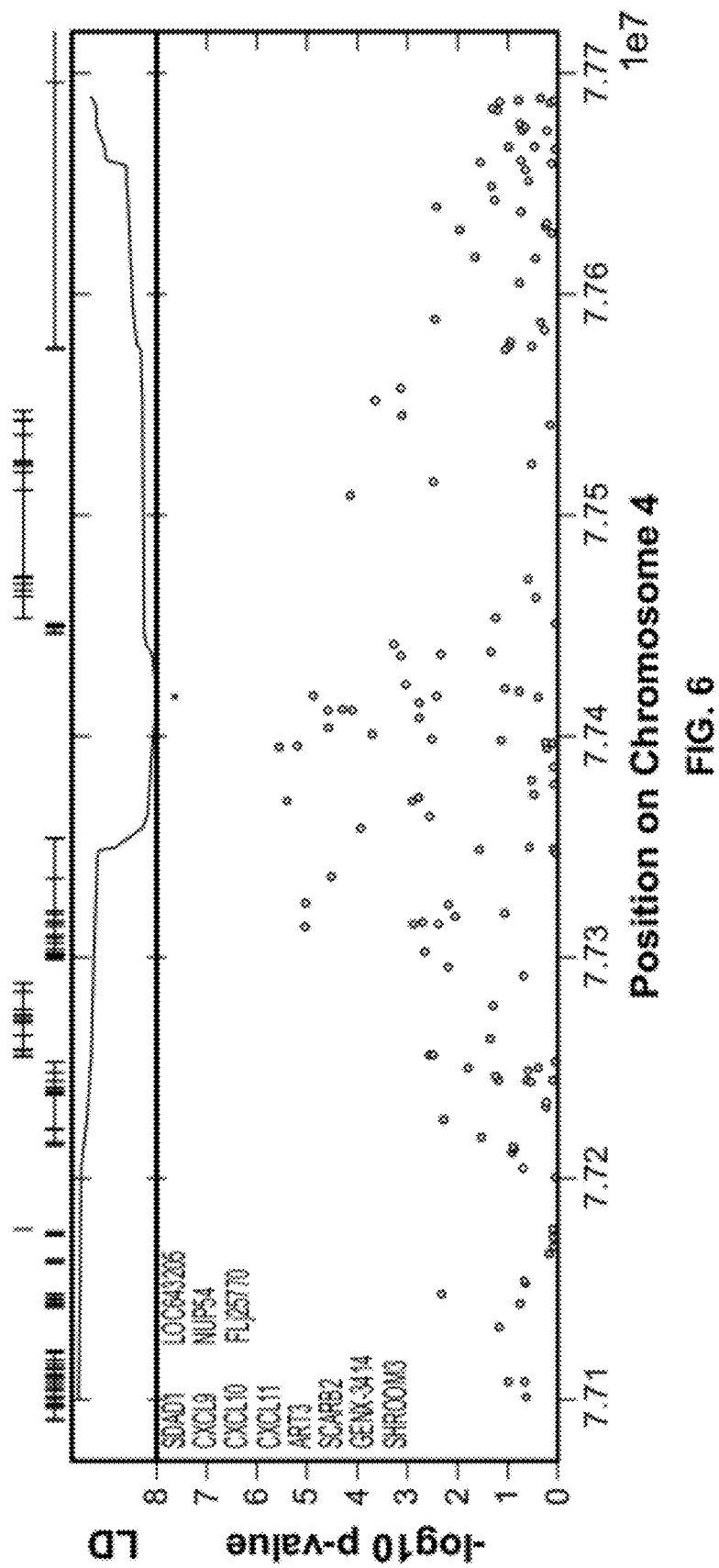
FIG. 6 depicts plots of the p-values surrounding significant SNPs around the SCARB2 region. SNPs with a p-value under 10 e-6 are shown.
Figure 7:
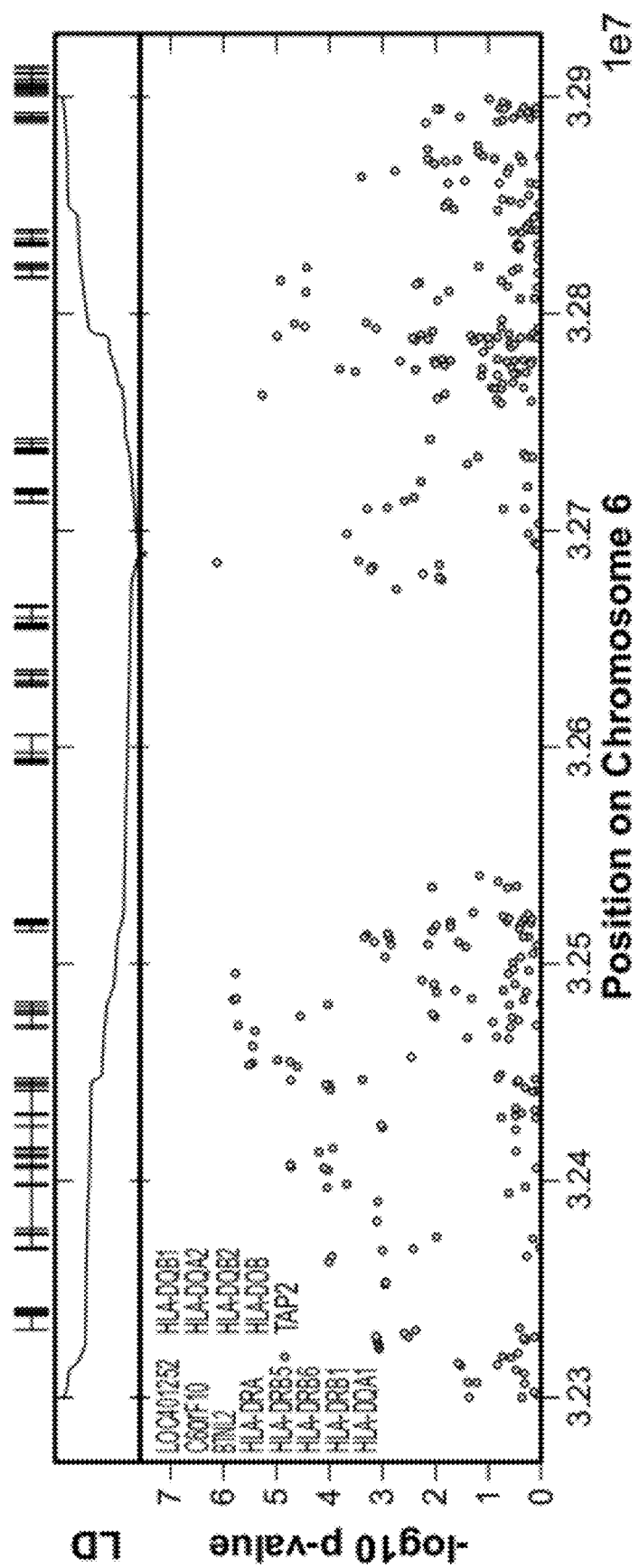
FIG. 7 depicts plots of the p-values surrounding significant SNPs around the HLA-DRB1 and HLA-DQA1 regions. SNPs with a p-value under 10 e-6 are shown.
Figure 8:
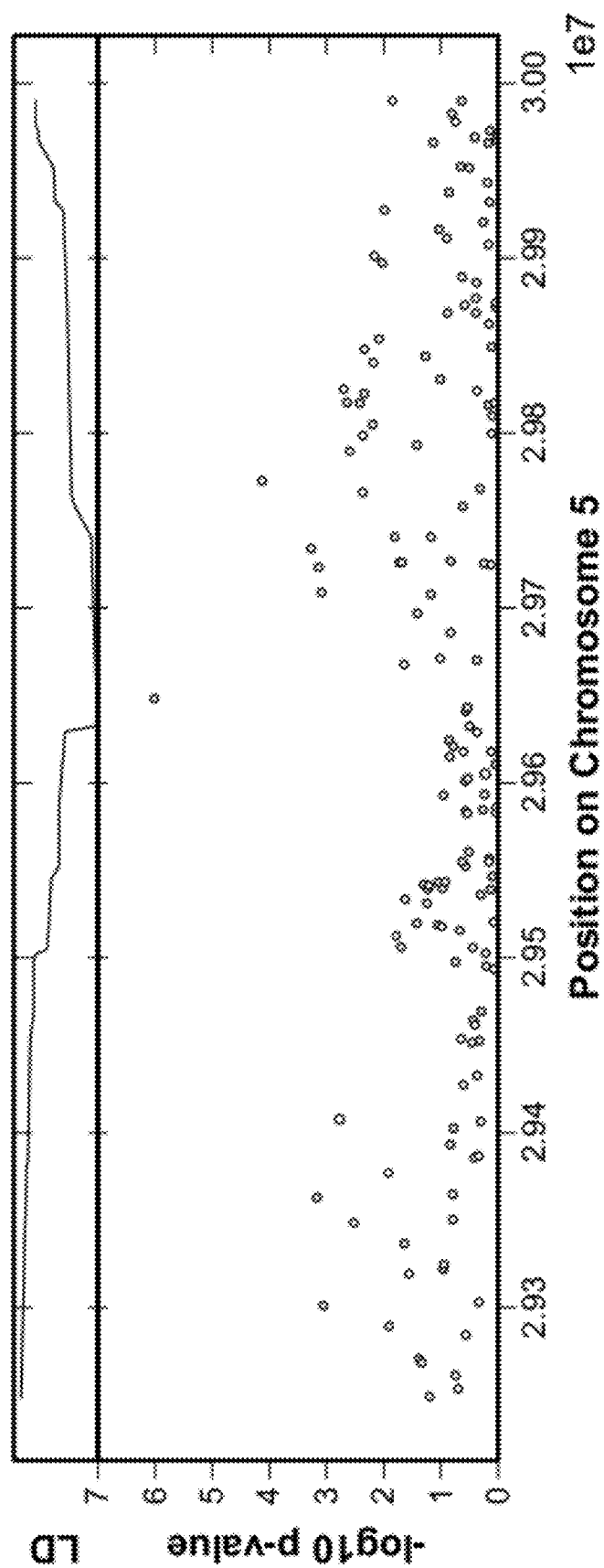
FIG. 8 depicts plots of the p-values surrounding significant SNPs around the LOC729862 region. SNPs with a p-value under 10e-6 are shown.

To correct for possible confounding due to ancestry, a subset of individuals having European ancestry was selected using multi-dimensional scaling (MDS) and a collection of ancestry informative markers. There was only very slight inflation present in the statistics (genomic control inflation factor of $\lambda \approx 1.04$, (Devlin and Roeder (1999) Genomic control for association studies, Biometrics 55(4): 997-1004). This indicates very high confidence that these associations are not just due to population. See FIG. 2, where the close concordance of p-values to expected shows no evidence of systematic bias.

E. LRKK2 modifying SNP rs11755699 (SEQ ID NO: 9). The LRRK2 G2019S mutation (rs34637584) is known to raise an individual's risk of developing PD by over 20-fold (Healy et al. (2008) *Phenotype, genotype, and worldwide genetic penetrance of LRRK2-associated Parkinson's disease: a case-control study*, Lancet Neurol. 7(7):583-590). Applicants conducted a genome-wide association study (GWAS) using a population of individuals identified as carriers of this mutation in the 23andMe database in order to find potential genetic modifiers (23andMe, Mountain View, Calif. 94040).

The GWAS was conducted in 60 people over the age of 50 who carried the LRRK2 G2019S mutation. Although by typical standards this may appear to be a small set in terms of a population size for a GWAS, the cohort represents one of the largest collections of G2019S positive people in the world, as the G2019S mutation is quite rare. The most significant association found in this analysis was the mutation rs11755699 (SEQ ID NO: 9), which lies in an intron of SGK1. It had a p-value (using Fisher's exact test) of under 10^-5.5, and an odds ratio of over 42 for not developing PD if one carried the C allele (T being the more common allele). Of the 20 people with G2019S and without PD, 10 of them had the C allele, as compared to the 0 or 1 that would be expected.

While this association wasn't significant genome-wide, it was the most significant among all the SNPs tested. Furthermore, rs11755699 (SEQ ID NO: 9) is intronic in SGK1 gene which is known to be associated with cell survival in neurodegenerative diseases such as PD (Stichel et al. (2005) *Sgk1, a member of an RNA cluster associated with cell death in a model of Parkinson's disease*, Eur J. Neurosci. 21(2):301-316; and Schoenebeck et al. (2005) *Sgk1, a cell survival response in neurodegenerative diseases*, Mol Cell Neurosci. 30(2):249-264.

The descriptions provided above are exemplary methods of carrying out the invention and are not intended to limit the scope of the invention in any way. One of ordinary skill in the art will appreciate alternates or modifications that may be made without departure from the breadth and the scope of the invention as set forth in the claims below.

What is claimed is:

1. A method for screening a human subject for susceptibility to Parkinson's Disease (PD), the method comprising:
obtaining a nucleic acid sample from the human subject;
determining which allele is present in the sample at the polymorphic nucleotide position of SNP rs10513789 (SEQ ID NO: 1); and
identifying the human subject as having an increased risk of developing PD if the subject has a T at the polymorphic nucleotide position of rs10513789 (SEQ ID NO: 1).

2. The method of claim 1 wherein determining the identity of the polymorphic allele(s) is by a process that includes one or more of: sequencing the polymorphic allele(s) in a genomic DNA isolated from the nucleic acid sample, hybridizing the polymorphic allele(s) or an amplicon thereof to an array, digesting the polymorphic allele(s) or an amplicon thereof with a restriction enzyme, or amplification of the polymorphic allele(s).

3. The method of claim 2, wherein the amplification comprises performing a polymerase chain reaction (PCR), reverse transcriptase PCR (RT-PCR), or ligase chain reaction (LCR) using a nucleic acid isolated from the biological sample as a template in the PCR, RT-PCR, or LCR.

4. The method of claim 1 wherein the sample is obtained from blood or saliva.

5. The method of claim 1, further comprising determining which allele is present in the sample at one or more of the polymorphic nucleotide positions selected from the group of SNPs consisting of rs6599389 (SEQ ID NO: 2), rs873785 (SEQ ID NO: 3), rs11248060 (SEQ ID NO: 4), rs6812193 (SEQ ID NO: 5), rs4130047 (SEQ ID NO: 6), rs7451962 (SEQ ID NO: 7) and rs4397141 (SEQ ID NO: 8).

6. A method for generating a prognosis of a human subject's susceptibility to Parkinson's Disease (PD), comprising:

obtaining a genomic sample from said human subject;
analyzing the genomic sample to determine which allele is present in the sample at the polymorphic nucleotide position of SNP rs10513789 (SEQ ID NO: 1);
storing the determined allele of the sample in a database that includes a set of information related to said subject;
correlating the determined allele with an association between the alleles of rs10513789 (SEQ ID NO: 1) and susceptibility to PD in the database;
generating a prognosis of the subject's susceptibility to PD based on the correlation; and
communicating the prognosis of susceptibility to a medical practitioner.

7. The system of claim 6 wherein the set of information related to said subject comprises family medical history, diet, exercise and medical history of said subject.

\* \* \* \* \*

SEQUENCE LISTING

```
<160> NUMBER OF SEQ ID NOS: 9

<210> SEQ ID NO 1
<211> LENGTH: 61
<212> TYPE: DNA
<213> ORGANISM: Homo sapiens

<400> SEQUENCE: 1
tgatggtttt tcaattttgt tatgttgata kgtactgcat gataccagat tacaaacagg    60
g                                                                   61

<210> SEQ ID NO 2
<211> LENGTH: 61
<212> TYPE: DNA
<213> ORGANISM: Homo sapiens

<400> SEQUENCE: 2
cccgccgtct ctgtctcctc actccccgcc rtttgttgct gcctcagctt ctgttttccc    60
c                                                                   61

<210> SEQ ID NO 3
<211> LENGTH: 61
<212> TYPE: DNA
<213> ORGANISM: Homo sapiens

<400> SEQUENCE: 3
tcgtgatccc ccttcgtctt tcaacacctc rgtgtttctc ttcccggtga acatctactc    60
g                                                                   61

<210> SEQ ID NO 4
<211> LENGTH: 61
<212> TYPE: DNA
<213> ORGANISM: Homo sapiens

<400> SEQUENCE: 4
cttgtgggtt cacacatagc tgtgaggaaa ytgaacagac cccctgaagc ctttgtcagc    60
t                                                                   61

<210> SEQ ID NO 5
<211> LENGTH: 61
<212> TYPE: DNA
```

<213> ORGANISM: Homo sapiens

<400> SEQUENCE: 5
atcagaacga ttctaggtga taatctttta yggtcagagt tttcaaaaat ggcagaaaca    60
t                                                                    61

<210> SEQ ID NO 6
<211> LENGTH: 61
<212> TYPE: DNA
<213> ORGANISM: Homo sapiens

<400> SEQUENCE: 6
cctactaagt tggggaaagc tggatttgaa ycctggtctg tcaaaatcca aaggccatgt    60
t                                                                    61

<210> SEQ ID NO 7
<211> LENGTH: 61
<212> TYPE: DNA
<213> ORGANISM: Homo sapiens

<400> SEQUENCE: 7
gcgctttatt tctaggaagg gcaggaattc rgaatccctc atcctgtccc cagctacctg    60
t                                                                    61

<210> SEQ ID NO 8
<211> LENGTH: 61
<212> TYPE: DNA
<213> ORGANISM: Homo sapiens

<400> SEQUENCE: 8
gcgctttatt tctaggaagg gcaggaattc rgaatccctc atcctgtccc cagctacctg    60
t                                                                    61

<210> SEQ ID NO 9
<211> LENGTH: 61
<212> TYPE: DNA
<213> ORGANISM: Homo sapiens

<400> SEQUENCE: 9
tgtgtcacag attcaaagct cttcgttccc ygaagtcctg ctactgtgac ttggaactct    60
c                                                                    61